United States Patent [19]

Tsuji et al.

[11] Patent Number: 4,916,072

[45] Date of Patent: Apr. 10, 1990

[54] PROCESS FOR THE FORMATION OF HUMAN-HUMAN HYBRIDOMA

[75] Inventors: Kimiyoshi Tsuji, Yokohama; Nobunao Ikewaki, Hatano, both of Japan

[73] Assignee: Idemitsu Kosan Co., Ltd., Tokyo, Japan

[21] Appl. No.: 31,671

[22] Filed: Mar. 30, 1987

[30] Foreign Application Priority Data

Mar. 28, 1986 [JP] Japan .................................. 61-70199

[51] Int. Cl.$^4$ ...................... C12N 5/00; A61K 39/395
[52] U.S. Cl. ............................ 435/240.27; 435/70.21; 435/172.2; 435/240.26; 435/948; 530/387; 530/809; 935/90; 935/100
[58] Field of Search .......... 435/172.2, 240.26, 240.27, 435/68, 948; 530/387; 935/809, 90, 100

[56] References Cited

U.S. PATENT DOCUMENTS 4,675,295  6/1987  Osawa et al. ..................... 435/172.2

FOREIGN PATENT DOCUMENTS 59-44325 of 1984 Japan .............................. 435/240.27

OTHER PUBLICATIONS

Carson et al., Advances in Immunol. 38:275, 296–7, (1986).
Kozbor et al.(a), PNAS 79:6651–55 (1982).
Kozbor et al.(b), Immunology Today 4(3):72–79 (1983).
Asada et al., Cell. Immunol. 77(1):150–60 (1983).
Higuchi et al., Cell. Immunol. 78(2):257–65 (1983).

*Primary Examiner*—Charles F. Warren
*Assistant Examiner*—Jasemine C. Chambers
*Attorney, Agent, or Firm*—Oblon, Spivak, McClelland, Maier & Neustadt

[57] ABSTRACT

A human-human hybridoma is formed by subjecting a transformed human cell to a proliferaton inhibitory treatment and then fusing the thus-treated human cell with a human antibody producing cell. A desired clone may be selected from the resultant fused cells by using an anti-HLA antibody.

2 Claims, 1 Drawing Sheet o— absorbance at 280 nm

☐ % of positive cells stained

PROCESS FOR THE FORMATION OF HUMAN-HUMAN HYBRIDOMA

BACKGROUND OF THE INVENTION

1. Field of the Invention

This invention relates to a process for the formation of a human-human hybridoma having an ability to produce a desired human antibody.

2. Description of the Prior Art

The usefulness of monoclonal antibodies has been confirmed not only in the field of immunology but also in many other fields. They are hence employed widely. However, since these antibodies are produced primarily with hybridoma originated from mouse cell, certain inherent limitations are obviously imposed on their application for the diagnosis and treatment of human.

Upon formation of a human monoclonal antibody, it is necessary to obtain a cell which has been challenged by a desired antigen and can produce a human antibody specific to the antigen. The in vivo antigenic stimulation is not feasible in human except for a certain class of antigens and there have not been established any method applicable to various antigens.

It is attempted to obtain permanently-established human cells by immortalization of antibody-producing cells, for example, by their fusion with human myeloma cells, their transformation with an Epstein-Barr virus (EBV) or the like and then to obtain a monoclonal antibody from the permanently-established human cells. Unlike in mouse lines, hybridomas or transformed cells having the ability of stable production of antibody have not been obtained in human lines for the time being.

There is hence a strong demand for the provision of permanently-established cells which can stably produce a desired human monoclonal antibody.

SUMMARY OF THE INVENTION

The present inventors have proceeded with a variety of investigation with a view toward obtaining a hybridoma from human cells. It has been found that a human-human hybridoma capable of producing a human monoclonal antibody stably can be obtained by subjecting a permanently-established human cell to a specific treatment and then fusing the thus-treated cell with a human antibody producing cell.

In one aspect of the invention, there is thus provided a process for the formation of a human-human hybridoma, which comprises subjecting a transformed human cell to a proliferation inhibitory treatment and then fusing the thus-treated human cell with a human antibody producing cell.

In another aspect of the invention, there is also provided a process for the formation of a human-human hybridoma, which comprises subjecting a transformed human cell to a proliferation inhibitory treatment, fusing the thus-treated human cell with a human antibody producing cell, and then selecting a clone from the resultant fused cells using an anti-HLA antibody.

In a further aspect of the invention, there is also provided a human-human hybridoma obtained by subjecting a transformed human cell to a proliferation inhibitory treatment and then fusing the thus-treated human cell with a human antibody producing cell.

In a still further aspect of the invention, there is also provided a human-human hybridoma deposited with IFO under IFO-50127.

In a still further aspect of the invention, there is also provided a monoclonal antibody produced by a human-human hybridoma which has in turn been obtained by subjecting a transformed human cell to a proliferation inhibitory treatment and then fusing the thus-treated human cell with a human antibody producing cell.

In a still further aspect of the invention, there is also provided a monoclonal antibody produced by a hybridoma deposited with IFO under IFO-50127.

The above-formed human-human hybridoma is extremely useful, since it produces the desired human monoclonal antibody in the culture supernatant when cultivated by a conventional technique. Incidentally, the above antibody can be purified and isolated by methods which are employed routinely in the art. For example, high performance liquid chromatography, affinity column chromatography and the like are mentioned as particularly suitable methods.

Comparing with ordinary methods, in this invention, human cells are fused at the high frequency and thus obtained human-human hybridoma clone stably produces monoclonal antibody for a long period.

In addition, the human monoclonal antibodies produced by the human-human hybridoma obtained in accordance with the process of this invention have lower alloantigenicity compared with monoclonal antibodies produced by hybridomas formed from animal cells and are therefore useful as therapeutic and diagnostic drugs.

BRIEF DESCRIPTION OF THE DRAWING

The above and other objects, features and advantages of the present invention will become apparent from the following description and the appended claims, taken in conjunction with the accompanying drawing, in which:

DETAILED DESCRIPTION OF THE INVENTION AND PREFERRED EMBODIMENTS

Figure 1:
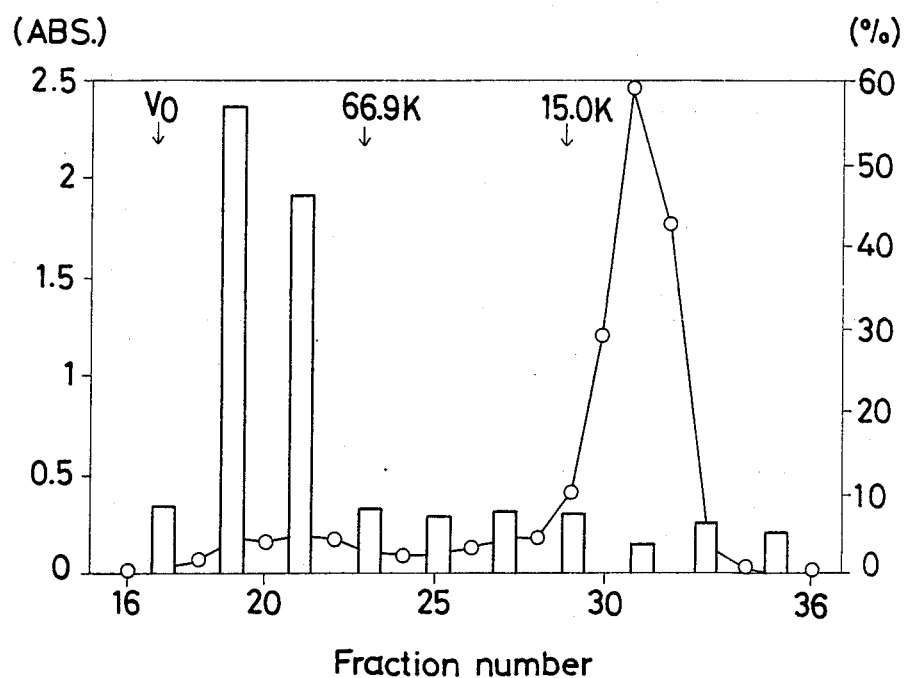
FIG. 1 diagrammatically shows the absorbance at 280 nm of effluent fractions of subclone (223·10·33) through a column of "Sephacryl S-300 Gel" and the percentage of positive cells stained by Ig.

For the practice of the process of this invention, it is necessary first of all to inhibit the proliferation of transformed human cells.

Illustrative examples of transformed human cells as a parent strain may include human tumor cells, for example, myeloma cells, leukemia cells, etc. They may also be obtained by transforming human cells in accordance with known methods, for example, infection with a virus or genetic recombination. As preferable human cells, may be mentioned human B cells, human liver cells, human spleen cells and human tonsil cells by way of example. Chemical treatment, exposure to radiation, etc. may be mentioned as methods for inhibiting the proliferation of such transformed human cells. Of these, a chemical treatment making either single or combined use of chemicals which inhibit the synthesis of proteins or RNA, for example, emetine, actinomycin D and the like is preferred. As to the concentration of a chemical to be employed upon conducting a chemical treatment, it should be determined in accordance with the kind of cells employed for fusion. However, it is generally preferred to use a chemical in such a concentration under which transformed human cells die completely in 7–10 days. The thus-obtained transformed human cells may be either heterozygous or homozygous. Taking the subsequent screening and the like into consideration, they may preferably be homozygous.

The transformed human cells which have been subjected to the proliferation inhibitory treatment are thereafter fused with antibody producing human cells.

As exemplary antibody producing human cells, may be mentioned human B cells, human plasma cells, human spleen cells, human lymph node cells, cultured human B cells, etc. Among these, human B cells are preferred. Antibody producing human cells separated from human tissue or blood may be used as they are. However, transformed cells may be used in view of technical readiness in operation of fusion etc. In this case, it is generally desirable to treat with an anti-HLA antibody subsequent to the fusion operation so that non-fused cells which produce antibody are excluded. The cell fusion can be conducted by a method known per se in that art, for example, a method making use of polyethylene glycol, a virus or the like, or the electric cell fusion method. As exemplary media useful for this cell fusion, may be mentioned RPMI 1640 medium, MEM medium and modified Dulbecco medium, their serum-added media, their serum-free media, and so on.

The thus-obtained human-human hybridoma is then subjected to a test for the determination of the desired antibody producing ability and also to cloning.

The assay of this antibody is effected by testing its reactivity against a sensitized antigen. It may be practiced following various methods employed generally for the assay of antibodies, for example, by the ELISA test [Meth. Enzymol., 70, 419-439(1980)], plaque test, spot test, agglutination reaction test, Ouchterlony's test, enzyme immunoassay (EIA), radioimmunoassay (RIA) or cytotoxic test ["Hybridoma Process and Monoclonal Antibody", R & D Planning K.K., 30-35, Mar. 5, 1982, etc.]. On the other hand, its cloning can be easily achieved, for example, by repeating a usual subcultivation and limiting dilution technique.

Having generally described the invention a more complete understanding can be obtained by reference to a certain specific example, which is provided herein for purposes of illustration only and is not intended to be limiting unless otherwise specified.

The present invention will hereinafter be described by the following Example.

EXAMPLE (i) Preparation of antibody producing B cells:

Peripheral blood was collected from a pregnant volunteer (SU: HLA-A2, —; Bw 46, 22; Cw 7, —; DR 4, 8), from which lymphocytes were separated by the ficoll-conlay gradient technique. T cells and B cells were separated by the rosette technique which employed neuramidase-treated SRBC, thereby obtaining B cells.

(ii) Sensitization of B cells with Epstein-Barr virus (EBV):

An EBV strain was prepared in a culture broth of EBV-transformed mormoset cells, B95-8 strain, which had grown in RPMI 1640/10% fetal calf serum (FCS), whereby a supernatant containing the virus was obtained. The supernatant was filtered twice. The virus strain was then added to 100 $\mu$l of a suspension which contained B cells at a concentration of $5 \times 10^4$ cells/100 $\mu$l, followed by incubation at 37° C. for 1 hour. Thereafter, 800 $\mu$l RPMI 1640/10% FCS was added. A fresh supply of the medium was added once every 3-4 days. Transformed B cells were found in about 2 weeks after the sensitization. These B cells will be called "EBV-SU".

(iii) Treatment of parent strain, EBV-transformed B lymphoblast cells (SA-1) with emetine and actinomycin D:

Homozygous SA-1 cells (HLA-A24, B7, C—, DR1, Dw1) were cultured in RPMI 1640/10% FCS. These cells were harvested at the growing phase, washed three times (1000 rpm, 10 minutes) in RMPI 1640, and adjusted to a concentration of $1 \times 10^6$ cells/ml. They were then treated at 37° C. for 2 with $5 \times 10^{-5}$ M/l emetine hydrochloride and 0.1 $\mu$g/ml actinomycin D. At these concentrations of emetine and actinomycin D, the proliferation of the SA-1 cells were completely inhibited. The cells were washed three times with RPMI 1640 in order to remove free emetine and actinomycin D, thereby obtaining proliferation-inhibited SA-1.

(iv) Cell fusion technique and growth conditions for fused cells:

EBV-SU cells were harvested and then washed three times with RPMI 1640. These cells were suspended in RPMI 1640 and mixed with the proliferation-inhibited SA-1 cells at a ratio of 10:1.

With continuous swirling, 0.25 ml 15% dimethyl sulfoxide (DMSO)-42.5% polyethylene glycol (PEG, m.w.: 1000) was added over 1 minute, followed by prewarming (at 37° C.). RPMI 1640 was added at a rate of 1 ml/min. The cells were pelleted for 10 minutes at 1000 rpm, suspended in RPMI 1640/10% FCS and then distributed into wells of microtiter plates. The suspension was prepared in such a way that the concentration of the proliferation-inhibited SA-1 cells became $5 \times 10^4$ cells per well. A fresh supply of the culture medium was added once every 2-3 days.

(v) Detection of HLA antigen and cloning of fused cells:

The HLA-DR surface antigen of the hybridoma was detected by the standard microlymphocytotoxicity test to clone fused cells having HLA-DR1, 4 and 8 antigens. Two hybridomas having HLA-DR1, 4 and 8 antigens are obtained from a million EBV-SU cells. In addition, the intended hybridoma was obtained by the limiting dilution technique.

(vi) Assay of immunoglobulin:

The culture supernatant of the hybridoma was investigated by the microlymphocytotoxicity test and immunofluorescence. Namely, the supernatant of the culture broth of the hybridoma was subjected to screening in accordance with the standard microlymphocytotoxicity test in which PBL and various cultured cell lines were used as target cells. The cells were adjusted to a concentration of $2 \times 10^6$ cells/ml. Cells (1 $\mu$l) were incubated together, with culture supernatant in Terasaki typing trays incubated for 1 hour at 37° C. Rabbit serum (5 $\mu$l, 1:2 dilution) was added as a source of complement and incubation was continued for 2 hours at room temperature. Cell viability was determined by eosin dye exclusion. The reactions were scored as follows:

| Score | Description | |
|---|---|---|
| 1 | Negative | (0-10% killed) |
| 2 | Weak negative | (11-20% killed) |
| 4 | Weak positive | (21-40% killed) |
| 6 | Positive | (41-80% killed) |
| 8 | Strong positive | (81-100% killed) |

The analysis of cell surfaces was conducted by an indirect immunofluorescence technique in which the culture supernatant of the hybridoma and fluorescein-conjugated goat anti-human Ig or rabbit anti-human Ig were used.

(vii) Ig class specific determination:

For the assay of the class determination of the antibody, an immunofluorescence technique making use of effluent fractions of a column of "Sephacryl S-300 Gel" was employed. Namely, the culture supernatant of the hybridoma was concentrated to a volume one tenth its original voluem. The concentrate was then caused to pass through the column of "Sephacryl S-300 Gel", so that the concentrate was fractionated. Using rabbit anti-human Ig (IgM or IgG) as a second antibody and fluorescence-conjugated goat anti-rabbit Ig (IgM or IgG) as a third antibody, the thus-fractioned sample was assayed against target cells, lung cancer cell line (QG56), by indirect immunofluorescence.

(viii) Detection of antibody secreting cells:

IgM or IgG secreting cells were detected using a reverse plaque assay in which protein A-conjugated SRBC and a monospecific anti-$\mu$ or anti-$\gamma$ antibody were used.

(ix) Characteristics of SA-1 cell line (parent strain):

EBV-transformed human B lymphoblast cell line (SA) was selected by a cloning technique in which Balb/C mouse thymocytes were used as a feeder layer (0.3 cell/well). Selected was a clone which grew faster. It was named "SA-1". The SA-1 cell line expressed HLA-A24, B7, C—, DR1 and Dw1 antigens and secreted IgG shown below in Table 1.

TABLE 1

| Cell line | HLA type | Number of plaque forming cells (PFC) | |
|---|---|---|---|
| | | IgM-PFC/$10^4$ | IgG-PFC/$10^4$ |
| SA-1 | A24,B7,C-DR1 | 0 | 1000 |

(x) Screening of anti-HLA reactivity of SU serum:

With respect of serum of a pregnant volunteer (SU), its reactivity against HLA (human leukoctye antigen) was subjected to screening by the standard microlymphocytotoxicity test. The antibody was cytotoxic to lymphoma cells of 8 normal volunteers and EBV-transformed homozygous typing cells. The specificity of this antibody however had no correlation with any of known HLA-A, B, C and DR locus antigens as shown next in Tables 2 and 3.

TABLE 2

| Cells of* normal volunteers | 1 T/B | 2 T/B | 3 T/B | 4 T/B | 5 T/B | 6 T/B | 7 T/B | 8 T/B |
|---|---|---|---|---|---|---|---|---|
| | +/− | −/+ | +/+ | +/− | +/− | +/− | +/+ | −/+ |

*HLA type

| | A | B | C | DR |
|---|---|---|---|---|
| 1 | A24 | B51.54 | C1 | DR4- |
| 2 | A2.24 | B39.46 | C1.3 | DR5- |
| 3 | A11.24 | B48.51 | C- | DR2.9 |
| 4 | A2.24 | B61 | C1 | DR8- |
| 5 | A2.24 | B39.61 | C7- | DR2.4 |
| 6 | A2.24 | B54.59 | C1 | DR4- |
| 7 | A2.24 | B46.51 | Cw46 | DR8.9 |
| 8 | A2.24 | B55.59 | C1- | DR4.9 |

TABLE 3

| | Homozygous typing cells | |
|---|---|---|
| | DR | |
| SA | 1 | + |
| TOK | 2 | + |
| JM190980 | 3 | + |
| WA | 4 | + |
| SUD | 4 | + |
| HOR | 6 | + |
| MANN | 7 | + |
| BAE | 8 | + |
| GDCL | 9 | + |

(xi) Characteristics of EBV-SU cell lines:

EBV-SU cell lines express HLA-A2-Bw-46 and 22Cw7DR4.8. These cell lines have been found to excrete IgM and IgG as shown below in Table 4.

TABLE 4

| Cell line | HLA type | Number of plaque forming cells (PFC) | |
|---|---|---|---|
| | | IgM-PFC/$10^5$ | IgG-PFC/$10^5$ |
| EBV-SU | A2-Bw46 22 Cw7 DR4.8 | 2800 | 1309 |

(xii) Assay of culture supernatant of hybridoma for various cells and cell lines:

The hybrid cells (223) derived from proliferation-inhibited SA-1 and EBV-SU express HLA-DR1, 4 and 8 antigens. These hybrid cells (223) were subjected to cloning (10 cells/well) to obtain a subclone (223·10·33). The subclone (223·10·33) produced a complement-dependent lymphocytotoxic antibody. This antibody had reactivity against human B lymphoblast cell lines and EBV-activated B blast cells. In addition, it also had reactivity against a lung cancer cell line (QG56) and a stomach cancer cell line (Kato III). However, the above antibody did not have reactivity against normal lymphatic tissue, T blast cells, leukemia T cells, myelomonocytes, Burkitt's lymphoma and pre-B leukemia (see Tables 5 and 6).

TABLE 5

| Cell type | Cell line | Reactivity of subclone (223 · 10 · 33) supernatant |
|---|---|---|
| Transformed B cell line | 1 SA | 8 |
| | 2 TOK | 8 |
| | 3 JM190980 | 8 |
| | 4 WA | 8 |
| | 5 SUD | 8 |
| | 6 MANN | 8 |
| | 7 BAE | 8 |
| | 8 B85 | 8 |
| | 9 Tani | 8 |
| | 10 K15 | 8 |

TABLE 5-continued

| Cell type | Cell line | | Reactivity of subclone (223 · 10 · 33) supernatant |
|---|---|---|---|
| | 11 | Ito | 8 |
| | 12 | Num | 6 |
| | 13 | U404 | 6 |
| Burkitt's | 14 | Daudi | 1 |
| lymphoma | 15 | P3HR-1 | 1 |
| | 16 | Ramos | 1 |
| | 17 | EB-3 | 1 |
| | 18 | Akata | 1 |
| | 19 | Raji | 1 |
| | 20 | BT-1 | 8 |
| | 21 | Namlwa | 1 |
| | 22 | HRIK | 1 |
| Pre-B leukemia | 23 | Nalm6 | 1 |
| Leukemia T cells | 24 | CEM | 1 |
| | 25 | Jurkat | 1 |
| Tumor cells | 26 | HL60 | 1 |
| | 27 | U937 | 1 |
| Acute lymphocytic leukemia | 28 | ALL-Kurume | 8 |
| | 29 | ALL-Kyto | 1 |
| Normal lymphatic tissue | 30 | Spleen cells | 1 |
| | 31 | Bone marrow cells | 1 |
| | 32 | PBL T cells | 1 |
| | | B cells | 1 |

TABLE 6

[QG56]

| Sample | % of positive cells stained |
|---|---|
| Control | 3.79 |
| 223 · 10 · 33 | 44.81 |

[Kato III]

| Sample | % of positive cells stained |
|---|---|
| Control | 2.19 |
| 223 · 10 · 33 | 17.49 |

(xiii) Analysis of subclone (223·10·33) Ig:

The specificity of the antibody class of subclone (223·10·33) Ig was determined by immuno-fluorescence (Table 7). Subclone (223·10·33) has been found to synthesize human IgM from fractions of its effluent through a column of "Sephacryl S-300 Gel" (FIG. 1.

TABLE 7

| | % of positive cells stained by | |
|---|---|---|
| Sample | IgM | IgG |
| Control | 1.37 | 0.98 |
| 223 · 10 · 33 | 46.89 | 3.93 |

(xiv) Antibody procuding ability of subclone (223·10·33):

The subclone (223·10·33) was cultured for 3 days at 37° C. in the medium consisted of RPMI 1640 supplemented with 10% FCS, 0.6% Hepes, 0.2% NaHCO$_3$, 100 units/ml of penicillin and 100 μg/ml of streptomycin. Initial cell concentration was $1 \times 10^5$ per ml and the final concentration was $3-4 \times 10^5$ per ml. Medium change was conducted every three days.

Antibody produced by the subclone (223·10·33) was determined by a microlymphotoxicity test in which B85, EBV-transformed B cell line, was used as target cells. The titer of antibody was expressed as maximum dilution rate of antibody solution at which over 90% of target cells were killed by its cytotoxicity.

The subclone (223·10·33) have been found to produce antibody stably for a long period as shown below in Table 8.

TABLE 8

| Number of subcultivation (times) | Period of subcultivation (days) | Titer of antibody (Maximum dilution number) |
|---|---|---|
| 30 | 90 | ×128 |
| 60 | 180 | ×256 |
| 120 | 360 | ×256 |

Having now fully described the invention, it will be apparent to one of ordinary skill in the art that many changes and modifications can be made thereto without departing from the spirit or scope of the invention as set forth herein.

We claim:

1. The antibody-producing human-human hybridoma deposited with IFO under IFO-50127.

2. A monoclonal antibody produced by the human-human hybridoma deposited with IFO under IFO-50127.

* * * * *